United States Patent [19]

Ross

[11] 4,130,581

[45] Dec. 19, 1978

[54] PREPARING J ACID BY FUSION USING PHENOLIC FLUXING AGENT

[75] Inventor: Lawrence J. Ross, Martinsville, N.J.

[73] Assignee: American Cyanamid Company, Stamford, Conn.

[21] Appl. No.: 838,780

[22] Filed: Oct. 3, 1977

[51] Int. Cl.$^2$ ............................................. C07C 143/66
[52] U.S. Cl. ................................................ 260/509
[58] Field of Search ......................................... 260/509

[56] References Cited

U.S. PATENT DOCUMENTS 458,285   8/1891   Kuzel .................................... 260/509

Primary Examiner—Joseph E. Evans
Attorney, Agent, or Firm—John L. Sullivan; Bruce F. Jacobs

[57] ABSTRACT

Amino J Acid is reacted with alkali to produce J Acid. The use of a phenolic compound as a fluxing agent for the reaction mixture permits the use of higher temperatures to produce high yields of J Acid in shorter reaction times.

4 Claims, No Drawings

PREPARING J ACID BY FUSION USING PHENOLIC FLUXING AGENT

This invention relates to an improvement in the process for the preparation of J Acid, 7-amino-4-hydroxy-2-naphthalenesulfonic acid, by fusing Amino J Acid, 6-amino-1,3-naphthalenedisulfonic acid, with an alkali hydroxide in the presence of a phenolic compound as a fluxing agent. The use of a phenolic fluxing agent results in high yields of J Acid in a shorter period of time than heretofore accomplished, without using high mole ratios of alkali hydroxide.

J Acid is a well-known dye intermediate as well as an additive that improves the stability and dyeability characteristics of colorants such as dyes and pigments.

It is well-known that J Acid can be prepared by reacting Amino J Acid with an alkali hydroxide, such as sodium hydroxide. However, the processes known thus far suffer from the necessity of conducting the reaction over an unusually long period of time, the need for highly pure starting materials, critical dependence of the reaction rate on the strength of the alkali hydroxide medium, by-product formation, and low yields. Some of the well-known processes for producing J Acid are described below.

The known reactions for the production of J Acid can be classified under two categories—the autoclave reaction and the open pot reaction. The autoclave reaction, in general, necessitates autoclaving the Amino J Acid with 50 percent caustic alkali for 11 hours at about 190° C. after a heating period of 5 to 7 hours. This reaction requires about 14.3 moles of the caustic alkali per mole of disodium salt of Amino J Acid. The BIOS open pot process (BIOS Document 1440/112/H/b/2, May 2, 1945; Leverkusen and BIOS Final Report 1157, pp. 37, 38) requires reacting a hot concentrated solution of the disodium salt of Amino J Acid with 72 percent caustic alkali for 7 to 8 hours at 187° C. following a heating period of 8 to 10 hours at 150° C. to 155° C. This reaction requires 3.75 moles of the caustic alkali per mole of the disodium salt of Amino J Acid. The open pot process of Nara et al. (Nara and Manabe, Kogyo Kagaki Zashi 72 (10), pp. 22858, 1969) utilizes 40 moles of a caustic alkali per mole of Amino J Acid and requires conducting the reaction at a caustic strength of 67.5 to 80 percent for a period of 4 to 5 hours at 170° C. The rate of reaction of this process is critically dependent upon the caustic strength because if the caustic strength drops below 70 percent the reaction rate is reduced substantially. It is anticipated that this reaction can be performed at lower ratios of caustic alkali to Amino J Acid than stated above provided the Amino J Acid is free from residual sulfuric acid and water.

It is an object of this invention to produce J Acid by reacting Amino J Acid with a caustic alkali over a shorter period of time than heretofore accomplished without adversely affecting the yeild.

Another object of this invention is to devise a process that does not necessitate the use of highly pure reactants.

A further object is to provide a process that gives a high yield of J Acid in a short time with a minimum of by-product formation.

These and other objects of this invention are accomplished by the process of the present invention, as described hereinafter.

SUMMARY OF THE INVENTION

This invention provides a process for the production of 7-amino-4-hydroxy-2-naphthalenesulfonic acid, and the alkali metal salts thereof, by fusing 6-amino-1,3-naphthalenedisulfonic acid, or alkali metal salts thereof, with a caustic alkali which is present in excess of that required for the completion of the reaction, at an elevated temperature, said fusing being effected in the presence of a phenolic compound fluxing agent.

The preferred embodiment of the present invention comprises a process wherein Amino J Acid is fused with an amount of sodium hydroxide up to a sixfold excess over that required for the fusion and for neutralizing the phenolic fluxing agent and any residual sulfuric acid present in the reactants used.

The advantages of the use of the phenolic fluxing agent are (1) the need for very high amounts of caustic soda is eliminated, (2) the use of the phenolic compound lowers the viscosity of the fusion mass and (3) the reaction can be conducted at higher temperatures, thus increasing the reaction rate.

DESCRIPTION OF PREFERRED EMBODIMENTS

This invention is based on the discovery that addition of phenolic compound, or an alkali metal salt thereof, results in complete conversion of Amino J Acid to J Acid at a temperature of about 220° C. to about 300° C., preferably 250° C. to 280° C. The duration of the fusion reaction is dependent on factors such as temperature, fluidity of the reaction mass, agitation, caustic concentration and stability of the chemical species. It is observed that the higher the fusion temperature the shorter the period of time required for the completion of the reaction and vice versa. For instance, at fusion temperatures above about 270° C. it is necessary to conduct the reaction for only 2 to 20 minutes, preferably 3 to 10 minutes, for the completion of the reaction. However, at fusion temperatures below about 270° C. it is necessary to conduct the reaction for at least 20 minutes, preferably 30 to 60 minutes, for the completion of the reaction. In general, the fusion reaction of the instant invention is complete if the reaction is conducted at 220° C. to 300° C. for about 30 minutes.

The preferred Amino J Acid alkali metal salts useful in the invention are the sodium and potassium salts.

The caustic alkali useful in the practice of the present invention is sodium hydroxide or potassium hydroxide or a mixture thereof. The preferred caustic alkali is sodium hydroxide because of its availability, cost, and ease of handling.

The phenolic compound fluxing agent useful in the practice of the present invention is any aromatic hydroxy compound. It is preferably selected from the group consisting of phenol, cresol, alkali metal salts thereof, and mixtures thereof. The preferred alkali metal salts are those of sodium and potassium. The phenolic compound acts as a fluxing agent by reducing the viscosity of the fusion mass, which in turn facilitates agitation of the mass and improves the mass transfer. This improvement in mass transfer obviates the need for high mole ratios of caustic alkali to Amino J Acid (see Nara and Manabe, supra). The improved mass transfer allows higher temperatures to be employed with consequent reduction in reaction time.

The fusion reaction of the instant invention can be carried out using varying amounts of the Amino J Acid, caustic alkali and the phenolic fluxing agent. The fusion reaction between Amino J Acid and a caustic alkali requires a total of 4 moles of the caustic alkali (2 moles for the initial formation of the alkali metal salt of the Amino J Acid and 2 moles to neutralize sulfur dioxide from the fusion reaction per mole of Amino J Acid). Excess caustic alkali is further required to neutralize any residual sulfuric acid present with the Amino J Acid and to react with the phenol fluxing agent which results in the formation of the corresponding alkali metal phenolate. The overall process involves the following reactions.

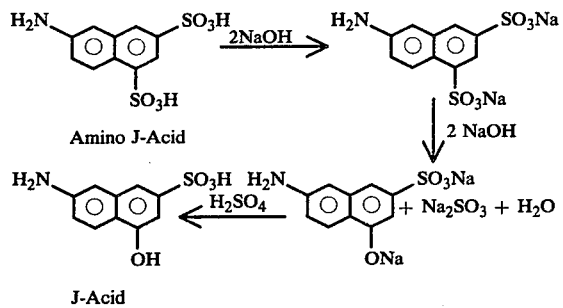

J-Acid

In accordance with the invention, the Amino J Acid is fused with an excess of caustic alkali, i.e. an excess of that required for all the reactions indicated above. It is preferably a threefold excess, calculated on the basis of the Amino J Acid, over that required for the fusion reaction, plus neutralizing the phenol fluxing agent and any sulfuric acid present. The amount of excess caustic alkali used can be over sixfold but such an excess has no attendant benefit. If the amount of caustic alkali used is far less than a threefold excess, the fusion reaction rate decreases considerably and hence the reaction requires longer periods of time.

The phenolic fluxing agent can be added in any amount. For achieving practical fusion reaction rates the amount of the phenolic fluxing agent used is in the range of from about 0.5 to about 5 moles, preferably from 2 to 3 moles, per mole of the Amino J Acid used. The fusion reaction rate and yield are not further improved by using the phenol fluxing agent in excess of 5 moles per mole of the Amino J Acid.

Although the invention is illustrated by the following example, it is believed apparent that there are numerous modifications in proportions of reaction ingredients and reaction conditions which are apparent within the spirit and scope of the invention.

EXAMPLE

A mixture of 43.2 grams of commercial Amino J Acid (70.2% real; 0.1 mole) containing 9.6% sulfuric acid (0.042 mole), 21.6 grams of phenol (0.23 mole) and 38.4 grams of sodium hydroxide (0.96 mole) was charged to a reaction vessel, preheated under a nitrogen atmosphere to 210° C. Then the temperature of the mixture was increased to 270° C. and the reaction mixture was held at 270° C. under a nitrogen atmosphere for 5 minutes. The reaction mixture was subsequently cooled to 145° C. and diluted with 50 ml. water. The diluted reaction mixture was added dropwise to a solution of 100 ml. of concentrated sulfuric acid admixed with 50 ml. of water preheated to 98° C. The resulting precipitate was filtered, washed repeatedly with 25 ml. portions of warm water maintained at 55° C., and dried. The dried solid on analysis was found to contain 16.5 grams of J Acid and 0.4 grams of Tobias Acid (that is, 2-amino-1-naphthalenesulfonic acid). The mother liquor on analysis was found to contain 2.9 grams of J Acid, 0.98 grams of Tobias Acid, and 1.44 grams of Amino J Acid. The overall yield of J Acid was 81 percent.

I claim:

1. In the process for preparing 7-amino-4-hydroxy-2-naphthalenesulfonic acid by the fusion reaction of 6-amino-1,3-naphthalenedisulfonic acid with a caustic alkali at an elevated temperature followed by cooling and neutralization with an acid, the improvement which comprises providing an effective amount of a phenolic compound selected from the group consisting of phenol, cresol and alkali metal salts thereof as a fluxing agent to the reaction mixture.

2. The process according to claim 1 wherein the amount of the fluxing agent present is from about 0.5 to about 5 moles per mole of the 6-amino-1,3-naphthalenedisulfonic acid.

3. The process according to claim 1 wherein the reaction is conducted at a temperature of from about 220° C. to about 300° C. and wherein the caustic alkali is present in up to about a sixfold excess over that required for the fusion reaction and for reacting with the phenolic compound fluxing agent and any residual sulfuric acid present therein.

4. The process according to claim 3 wherein the reaction is conducted at a temperature of from about 270° C. to about 300° C. for a period of about 3 to about 10 minutes.

* * * * *